US009187576B2

(12) United States Patent
Prestwich (10) Patent No.: US 9,187,576 B2
(45) Date of Patent: Nov. 17, 2015

(54) DEUTERIUM-ENRICHED HYALURONAN (71) Applicant: Deuteria Agrochemicals, LLC, Eastsound, WA (US)

(72) Inventor: Glenn Prestwich, Eastsound, WA (US)

(73) Assignee: Deuteria Biomaterials, LLC, Eastsound, WA (US)

( * ) Notice: Subject to any disclaimer, the term of this patent is extended or adjusted under 35 U.S.C. 154(b) by 0 days.

(21) Appl. No.: 14/552,507

(22) Filed: Nov. 25, 2014

(65) Prior Publication Data

US 2015/0148310 A1 May 28, 2015

Related U.S. Application Data (60) Provisional application No. 61/930,273, filed on Jan. 22, 2014, provisional application No. 61/908,404, filed on Nov. 25, 2013.

(51) Int. Cl.
*C08B 37/00* (2006.01)
*A61K 31/728* (2006.01)
*C08B 37/08* (2006.01)

(52) U.S. Cl.
CPC ........... *C08B 37/0072* (2013.01); *A61K 31/728* (2013.01)

(58) Field of Classification Search
None
See application file for complete search history.

(56) References Cited

U.S. PATENT DOCUMENTS

| | | | |
|---|---|---|---|
| 7,449,171 B2 * | 11/2008 | Hellerstein | 424/9.1 |
| 7,811,806 B2 | 10/2010 | Sloma et al. | |
| 2006/0073178 A1 | 4/2006 | Giampapa | |
| 2006/0105022 A1 | 5/2006 | Yokokawa et al. | |
| 2010/0184720 A1 | 7/2010 | Molliard et al. | |
| 2010/0210587 A1 | 8/2010 | Matsumoto | |
| 2010/0317616 A1 | 12/2010 | Prestwich et al. | |

OTHER PUBLICATIONS

Li et al., "A stable isotope method for the simultaneous measurement of matrix synthesis and cell proliferation in articular cartilage in vivo" Osteoarthritis and Cartilage (2009) vol. 17 pp. 923-932.*
Holmes et al., "Hyaluronic acid in human articular cartilage: Age-related changes in content and size" Biochem. Journal (1988) vol. 250 pp. 435-441.*
Pavasant et al., "Hyaluronan contributes to the enlargement of hypertrophic lacunae in the growth plate" Journal of Cell Science (1996) vol. 109 pp. 327-334.*
Kogan, G. et al., Hyaluronic Acid: A Biopolymer with Versatile Physico-Chemical and Biological Properties, Handbook of Polymer Research: Monomers, Oligomers . . . : 2007, Chapter 31, pp. 393-439.
Greenwald, Robert A. et al., Effect of Oxygen-Derived Free Radicals on Hyaluronic Acid, Arthritis and Rheumatism, 1980, 23(4), 455-63.
Hawkins, Clare L. et al., Direct Detection and Identification of Radicals Generated During the Hydroxyl Radical-Induced Degradation of Hyaluronic Acid and Related Materials, Free Radical Biology & Medicine 1996, 21(3), 275-90.
Sodium Hyaluronate Ophthalmic Solution 0.18% NDA 22-358 FDA Advisory Committee Briefing Document Jun. 2009.
Vazquez, Jose A. et al., Hyaluronic acid production by Streptococcus zooepidemicus in marine by-products media from mussel processing wastewaters and tuna peptone viscera, Microbial Cell Factories 2010, 9(46), 1-10.
Boeriu, Carmen G. et al., Production Methods for Hyaluronan, International Journal of Carbohydrate Chemistry 2013, Article ID 624967, 1-14. http://dx.doi.org/10.1155/2013/624967.
Kim, Jeong-Hyun et al., Selection of a Streptococcus equi mutant and optimization of culture conditions for the production of high molecular weight hyaluronic acid, Enzyme and Microbial Technology 1996, 19, 440-5.
Yu, Huimin et al., Metabolic engineering of *Escherichia coli* for biosynthesis of hyaluronic acid, Metabolic Engineering 2008, 10, 24-32.
Mao, Zichao et al., Recombinant Synthesis of Hyaluronan by *Agrobacterium* sp., Biotechnol. Prog. 2007, 1038-42.
PCT/US2014/067201, Feb. 12, 2015, International Search Report and Written Opinion of the ISA (corresponding PCT application).
Hill, Shauna et. al., Small amounts of isotope-reinforced polyunsaturated fatty acids suppress lipid autoxidation, Free Radical Biology and Medicine,2012, 53, 893-906.

* cited by examiner

*Primary Examiner* — Eric Olson
(74) *Attorney, Agent, or Firm* — Vance Intellectual Property, PC (57) ABSTRACT The present invention generally relates to deuterium-enriched hyaluronan, d-HA, compositions containing the same, methods of using the same, and methods for making the same.

26 Claims, 4 Drawing Sheets

DEUTERIUM-ENRICHED HYALURONAN

FIELD OF THE INVENTION

The present invention generally relates to deuterium-enriched hyaluronan, compositions containing the same, methods of using the same, and methods for making the same.

BACKGROUND OF THE INVENTION

Hyaluronan, also called hyaluronic acid or hyaluronate or abbreviated HA, is a naturally occurring anionic, non-sulfated glycosaminoglycan whose repeating disaccharide is composed of β-(1,3)-D-glucuronic acid (left-hand portion below)(glucuronic acid) (GlcUA) and β-(1,4)-N-acetyl-D-glucosamine (right-hand portion below)(N-acetyl glucosamine)(GlcNAc).

HA is found in numerous places in humans and animals, including the vitreous humor of the eyes, the skin, the extracellular matrices of virtually all tissues, and synovial fluids of articular joints (e.g., the knee). The presence of HA is crucial during embryonic development for proper organogenesis and for scar-free healing in the fetus. The molecular weight (MW) of naturally occurring HA widely varies depending on its location and can be from about 0.200 to 10 MDa (million Daltons). The half-life of HA also widely varies depending on its location and can last from hours in synovial fluid to weeks in the extracellular matrix.

HA and its many chemical derivatives have multiple commercial uses that are typically dependent upon the MW of the HA. High MW HA, e.g., >0.5 MDa, is used for wound healing after cataract surgery (e.g., via ophthalmic injections) and as a visco-supplement to provide cushioning and lubrication and to reduce the pain of osteoarthritis in knees or other joints (e.g., via intra-articular injections). Other uses of HA and its chemical derivatives include wound healing in general, adhesion prevention after surgery, cell engineering, and in cosmetics (e.g., skin moisturizers).

While the viscoelastic properties of high MW HA provide lubrication to joints and protect sensitive tissues during and after surgery, these properties are lost when HA is degraded in vivo (e.g., enzyme or radical degradation). Lower MW HA can actually be inflammatory or angiogenic instead of anti-inflammatory or anti-angiogenic. The degradation of high MW and also lower MW HA results from naturally occurring hyaluronidases. In addition, substantial degradation also results from oxidation, mostly likely through hydroxyl radicals and a variety of reactive oxygen species (ROS) that can be produced as part of the pathology of inflammatory diseases. This has been reviewed in, for example, by G. Kogan, L. Soltes, R. Stern, and R. Mendichi, "Hyaluronic acid: a biopolymer with versatile physico-chemical and biological properties: In: Handbook of Polymer Research: Monomers, Oligomers . . . (R. A. Pethrick et al, Eds.), pp 393-439 (2007) Nova Science Publishers.)

Numerous solutions have been devised to slow the in vivo degradation of HA and to modify its chemical, physical, and biological properties. These solutions typically involve chemical modification of the HA, including for example crosslinking by chemical or photochemical means. Examples of crosslinking agents include thiols (with thiols and electrophiles such as acrylates), methacrylates, tyramines, formaldehyde (Hylan-A), divinyl sulfone (Hylan-B), biscarbodiimides (Monovisc), and cinnamate dimers (Gel-One). Other solutions include modifying HA with a large group such as a polypeptide to induce cell attachment or self-assembly into a hydrogel. Unfortunately, chemical modifications often times lead to side effects and foreign body reactions not observed with unmodified HA, which has naturally low immunogenicity and low toxicity. The chemistry and biology of HA, the medical uses of HA, and the scope of chemical modifications employed in research and medical products are the subject of recent reviews, including: J. W. Kuo and G. D. Prestwich, "Chapter 73. Hyaluronic Acid" in Materials of Biological Origin—Materials Analysis and Implant Uses, *Comprehensive Biomaterials*, Vol. 2 (eds. P. Ducheyne, K. Healy, D. Hutmacher, J. Kirkpatrick), Elsevier pp. 239-259 (2011) and J. Burdick, G. D. Prestwich, "Hyaluronic Acid Hydrogels for Biomedical Applications", *Advanced Materials* 23, H41-H56 (2011).

In view of its numerous uses and its known susceptibility to degradation, there is a need for improved HA and HA-containing compositions.

SUMMARY OF THE INVENTION

In an aspect, the present invention provides novel deuterium-enriched HA (d-HA) and compositions containing the same.

In another aspect, the present invention provides a novel method of making d-HA.

In another aspect, the present invention provides novel methods of using d-HA, e.g., to treat osteoarthritis.

These and other aspects, which will become apparent during the following detailed description, have been achieved by the inventor's discovery that HA can be enriched and stabilized with deuterium.

BRIEF DESCRIPTION OF THE DRAWINGS

FIG. 1: Mass spectrogram of HA4 for G, G1 and G6 starting materials. The molecular weight of HA4 (4 HA monosaccharaide units) derived from unenriched glucose (G) and enriched glucoses (G1 and G6) are shown.

DETAILED DESCRIPTION OF THE INVENTION

Deuterium (D or $^2$H) is a stable, non-radioactive isotope of hydrogen and has an atomic weight of 2.0144. Hydrogen naturally occurs as a mixture of the isotopes $^1$H (hydrogen or protium), D ($^2$H or deuterium), and T ($^3$H or tritium). The natural abundance of deuterium is 0.015%. One of ordinary skill in the art recognizes that in all chemical compounds with a H atom, the H atom actually represents a mixture of H and D, with about 0.015% being D. Compounds with a level of deuterium that has been enriched to be greater than its natural abundance of 0.015%, should be considered unnatural and, as a result, novel over their non-enriched counterparts. Thus, the present invention relates to a deuterium enriched compound or compounds wherein their level of deuterium is greater than naturally occurring un-enriched compounds.

All percentages given for the amount of deuterium present are mole percentages.

When a variable is not accompanied by a definition, the previous definition of the variable controls.

Depolymerization by reactive oxygen-derived species is a major cause of loss of the desirable viscoelastic properties of HA in inflamed tissues. Depolymerization can also occur as a result of strand scission by hydroxyl radical and or ROS-derived species. Without being bound by any specific mechanism, depolymerization may also involve strand breakage due to bond cleavage within one of the disaccharide unit sugar molecules, initiated generally by abstraction of carbon-attached hydrogen atoms (e.g., the anomeric hydrogens and other hydrogens attached to carbons in the polysaccharide backbone).

The deuterium-enriched HA (d-HA) provided herein has an increased stability (e.g., reduced degree or slower rate of depolymerization) as compared to naturally occurring or un-enriched HA. Without being limited by a particular theory, this increased stability most likely occurs when at least some (and perhaps all) of the carbon-attached hydrogens of HA (e.g., the anomeric hydrogens and other hydrogens attached to carbons in the polysaccharide backbone) are replaced with deuterium. The anomeric positions are those at the reducing end of each sugar at either a ketal or hemiketal linkage, and, without being bound by any specific mechanism, chain cleavage is likely to occur when radicals are formed at these sites. Replacement of the carbon-attached hydrogens of HA, including the anomeric hydrogens and other readily abstracted hydrogen atoms along the polysaccharide backbone, with deuterium provides a stronger bond that is more resistant to free radical formation at the deuterated site, thereby reducing degradation; therefore d-HA is more resistant to degradation (e.g., by radical-induced depolymerization) than unenriched HA.

The more stable HA of the present invention not only allows for compositions with longer shelf lives (e.g., ophthalmic, osteoarthritic, and infant milk formula), but also provides a HA that will maintain its in vivo properties longer. These more stable HA molecules are advantageous as the stability is obtained without chemical crosslinking. Thus, the deuterium-enriched HA molecules of the present invention not only have desired biological properties of native HA, but they lack the off-target inflammatory properties resulting from allergic or foreign body responses to non-native chemistry due to the crosslinker.

(A) In an aspect, the present invention provides a novel deuterium-enriched hyaluronan, d-HA, of the formula:

or a pharmaceutically acceptable salt thereof;
wherein:
the d-HA has a molecular weight selected from about 15 kDa (kilo Daltons) to about 10 MDa (million Daltons);
each non-$R^{D/D1}$ H is independently hydrogen or deuterium; and, each $R^D$ and $R^{D1}$ is independently hydrogen or deuterium, provided that at least 1% of the total number of $R^D$ and $R^{D1}$ groups present are D.

(A1) In another aspect, the present invention provides a novel deuterium-enriched hyaluronan, d-HA$_B$, of the formula:

or a pharmaceutically acceptable salt thereof;
wherein:
the d-HA has a molecular weight selected from about 15 kDa (kilo Daltons) to about 10 MDa (million Daltons);
each non-$R^{D/D1}$ H is independently hydrogen or deuterium; and,
each $R^D$ and $R^{D1}$ is independently hydrogen or deuterium, provided that at least 1% of the total number of $R^{D1}$ groups present are D.

(A2) In another aspect, the present invention provides a novel deuterium-enriched hyaluronan, d-HA, of the formula d-HA$_{B1}$:

or a pharmaceutically acceptable salt thereof;
wherein:
each non-$R^{D1}$ H is independently hydrogen or deuterium; and,
each $R^{D1}$ is independently hydrogen or deuterium, provided that at least 1% of the total number of $R^{D1}$ groups present are D.

(B) In another aspect, the present invention provides a novel deuterium-enriched hyaluronan, d-HA, of the formula d-HA$_1$:

or a pharmaceutically acceptable salt thereof;

wherein:

each non-$R^{D1}$H is independently hydrogen or deuterium; and, each $R^{D1}$ is independently hydrogen or deuterium, provided that at least 1% of the total number of $R^{D1}$ groups present are D.

(C) In another aspect, the present invention provides a novel deuterium-enriched hyaluronan, d-HA, of the formula d-HA$_2$:

or a pharmaceutically acceptable salt thereof;
wherein:

each non-$R^D$ H is independently hydrogen or deuterium; and, each $R^D$ is independently hydrogen or deuterium, provided that at least 1% of the total number of $R^D$ groups present are D.

(D) In another aspect, the present invention provides d-HA of clauses (A)-(C) wherein the molecular weight, MW, of d-HA is selected from (a) about 0.1 MDa to about 5 MDa, (b) about 0.5 MDa to about 3 MDa, (c) about 1 MDa to about 2.5 MDa, (d) about 15 kDa to about 100 kDa, and (e) about 15 kDa to about 35 kDa.

(E) In another aspect, the present invention provides d-HA of clauses (A)-(C)(whenever "(A)–" is mentioned, it includes A1 and A2) wherein the molecular weight of d-HA is selected from: about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, to about 100 kDa and about 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, to about 10 MDa.

(F) In another aspect, the present invention provides d-HA of clauses (A)-(E) wherein the % of the total number of $R^D$ and/or $R^{D1}$ groups present in d-HA that are D is selected from (a) 1-50%, (b) 5-90%, (c) 10-90%, (d) 20-90%, (e) 30-90%, (f) 40-90%, (g) 50-90%, (h) 10-50%, and (i) 25-50%.

(G) In another aspect, the present invention provides d-HA of clauses (A)-(E) wherein the % of the total number of $R^D$ and/or $R^{D1}$ groups present in d-HA that are D is selected from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, to 100%.

(H) In another aspect, the present invention provides a novel pharmaceutical composition, comprising: d-HA according to the present invention (e.g., clauses (A)-(G)) and a pharmaceutically acceptable excipient.

(I) In another aspect, the present invention provides a novel composition for treating osteoarthritis in a patient, comprising: a therapeutically effective amount of a d-HA of the present invention (e.g., clauses (A)-(G)) and a pharmaceutically acceptable excipient, wherein the composition is suitable for injection into a patient's joint. The joint is an articular joint such as the knee, hip, shoulder, elbow, wrist, ankle, digit, or facet joint.

(J) In another aspect, the present invention provides a novel osteoarthritis composition of d-HA (e.g., clauses (A)-(G)). The osteoarthritis composition is housed in a pre-filled sterile-packed syringe containing from 0.5 mL to 12 mL of d-HA in a sterile phosphate-buffered saline (alternatively a similar sterile aqueous solution known in the art to be suitable for intra-articular injection can be used). The concentration of d-HA is from 0.2% w/w to 5% w/w. The size of the d-HA is from about 50 kDa to about 5 MDa.

(K) In another aspect, the concentration of d-HA is from 1% w/w to 3% w/w. The size of the d-HA is from about 250 kDa to about 2.5 MDa.

(L) In another aspect, the present invention provides a novel ophthalmic composition, comprising: d-HA of the present invention (e.g., clauses (A)-(G)) and a pharmaceutically acceptable excipient, wherein the composition is suitable for application to or injection into a patient's eye. One aspect of the ophthalmic composition is to improve the eye environment or improve the feeling of the eye. Another aspect of the ophthalmic composition is to retard depolymerization of HA in the eye to maintain the physical structure of the eye and physiological environment inside the eye. Another aspect of the ophthalmic composition is to have the d-HA act as a supplement or replacement for the vitreous humor inside the eye. Still another aspect of the ophthalmic composition is for the d-HA to be used in place of HA during ophthalmic surgery. Still another aspect is to deliver drugs by introvitreal injection. This type of injection is expected to benefit persons suffering from age-related macular degeneration (AMD).

(M) In another aspect, the present invention provides a novel artificial tears composition, comprising: d-HA according to the present invention (e.g., clauses (A)-(G)) and an excipient suitable for eye drops. Such excipients can include water, saline, and buffers as well as additional lubricants (e.g., polyethylene glycol 400), preservatives (e.g., sodium chlorite and sodium perborate), and additional acids and salts (e.g., boric acid, sodium borate, calcium chloride, magnesium chloride, and potassium chloride). This type of composition can be used to treat the symptoms of dry eye or other sources of ocular irritation or corneal injury in patients.

(N) In another aspect, the present invention provides a novel ophthalmic composition of d-HA. The d-HA of the present invention (e.g., clauses (A)-(G)) is formulated as eye drops at a concentration of from 0.05% to 1% w/w in a sterile ophthalmic solution known to those skilled in the art. Additional examples of the amount of d-HA present include from 0.1-0.5% w/w and from 0.15-0.25% w/w.

(O) In another aspect, the present invention provides a novel milk composition (e.g., infant formula), comprising a d-HA of the present invention (e.g., clauses (A)-(G)) wherein the weight of the d-HA is from about 15 kDa to about 100 kDa.

(P) In another aspect, the present invention is formulated into a novel topical anti-wrinkle and anti-aging moisturizing cream, ointment, gel, serum, hydrogel patch, or liposome preparation, comprising: d-HA according to the present invention (e.g., clauses (A)-(G)), water, and cosmetically acceptable excipients and actives. If a d-HA salt is used, it can be a cosmetically acceptable salt.

(Q) Examples of excipients for compositions of the present invention (e.g., clauses (H)-(P)) are those typically used for un-enriched (naturally occurring) HA and include water (e.g., when using a sodium or potassium salt of d-HA), physiological saline, sodium chloride, citric acid, and buffers (e.g., phosphate buffers including monobasic phosphate, dibasic phosphate, dibasic phosphate dodecahydrate).

(R) In another aspect, the pH of a composition of the present invention (e.g., clauses (H)-(Q)) is from 6.0-8.0. Additional examples of the pH include from 6.8-7.8. Further examples include 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, to 8.

(S) The weight of d-HA present in a composition of the present invention (e.g., clauses (H)—(R)) will depend on its use (e.g., osteoarthritic or ophthalmic). Examples include 0.1 to 100 mg. Additional examples include (a) 0.1-10 mg, (b) 10-50 mg, and (c) 10-25 mg. Further examples include 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, to 100 mg.

(T) The weight of d-HA present can also be expressed in terms of the weight percentage present. Examples of the weight % of d-HA present in a composition of the present invention (e.g., clauses (H)—(R)) include from 0.1-99%. Additional examples include (a) 0.1-5 wt %, (b) 0.1-1 wt %, and (c) 1-50 wt %. Further examples include 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, to 95 wt %.

(U) Examples of pharmaceutically or cosmetically acceptable salts for the d-HA of the present invention (e.g., clauses (A)-(T)) include for example sodium, potassium, ammonium, alkylammonium, calcium, lithium, manganese, magnesium, zinc, and cobalt salts.

(V) In another aspect, the present invention provides a novel prefilled container, comprising a d-HA of the present invention (e.g., clauses (A)-(G)) or a d-HA composition of the present invention (e.g., clauses (H)-(U)). Examples of prefilled containers include syringes (e.g., for an osteoarthritic or ophthalmic indication), eye drop bottles (e.g., for artificial tears), and a cream container, gel, hydrogel patch, or other cosmetically useful container or device (e.g., for a cosmetic composition). Examples of the volume of the syringes include 1, 2, 3, 4, 5, 6, 7, 8, 9, 10, 11, 12, 13, 14, 15, 16, 17, 18, 19, 20, 25, 30, 35, 40, 45, to 50 mL. Examples of the volume of the syringes also include 0.1, 0.2, 0.3, 0.4, 0.5, 0.6, 0.7, 0.8, 0.9, to 1 mL. Examples of the volume of the eye drop bottles include 0.5, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 350, 400, 450, to 500 mL. Examples of the volume of the eye drop bottles also include 0.4, 0.5, 0.6, 0.7, 0.8, 0.9, to 1 mL.

(W) In another aspect, the present invention could include a hydrogel patch for iontophoretic delivery of d-HA of the present invention (e.g., clauses (A)-(G)) into the skin, or a liposomal formulation with skin-penetrating peptides for delivery of d-HA into the skin, or a composition with other cosmetically acceptable peptides or transdermal delivery facilitating agents known in the art to deliver HA into the dermis and epidermis to reduce the depth and severity of wrinkles in aging or sun-damaged skin.

(X) The d-HA of the present invention (e.g., clauses (A)-(G)) can replace HA or cross-linked HA in applications for treating patients including: (a) treating osteoarthritis; (b) preventing post-operative surgical adhesions of tissue; (c) viscosupplementation in both humans and animals (e.g., equine, canine, and feline); (d) aiding in ophthalmic surgery, such as cataract removal, intraocular lens implantation, glaucoma filtering surgery, corneal transplantation, vitrectomy, and retinal reattachment; (e) scaffolding for tissue engineering in vitro or guided tissue regeneration or augmentation in vivo; (f) use as coatings for medical devices (e.g., catheters, guidewires, and stents); (g) promoting attachment of an in vitro fertilized embryo to the uterine wall; (h) induce tissue healing postoperatively; (i) induce or speed wound healing; (j) use as a dermal filler; (k) use as a controlled release medium (e.g., as a matrix or parenteral depot); (l) excipient for ophthalmic formulations; (m) ophthalmic moisturizer or humorous replacement; (n) protecting chondrocytes against oxidative damages, wherein the damages are caused by reactive oxygen; (O) slowing, attenuating, mitigating, and/or ameliorating the loss of bone mineral density in a vertebrate patient; (p) slowing, attenuating, mitigating, and/or ameliorating the formation of osteophytes in a vertebrate patient; (g) a component of a topical anti-wrinkle and anti-aging moisturizing cream, hydrogel patch, liposome or other cosmetic preparation; (q) administering as a drug pre-sensitizer and chemo-sensitizer in the treatment of disease, specifically chemotherapy; (r) regulating vascular permeability in a patient having symptoms of or diagnosed with a disease or condition involving increased vascular permeability (e.g., acute lung injury (ALI), acute respiratory distress syndrome (ARDS), atherosclerosis, macular degeneration, capillary leakage syndrome, and sepsis); (s) entraining and delivering cancer chemotherapeutic drugs by intravenous or intratumoral administration, thereby increasing delivery of the cytoxic drug to the tumor or metastasis site while reducing undesired side effects; (t) promoting wound repair or preventing adhesions in tympanic membrane repair, otological surgery, or rhinoscopic surgery; (u) preventing or repairing damage to the vocal folds by injection into the vocal folds; (v) providing a bulking agent for urinary incontinence by injection into the urinary sphincter muscle; (w) vehicle for drug delivery into the eye; (x) for use in the treatment of age-related macular degeneration (AMD); and (y) for intravitreal injection as a vitreous supplement and/or replacement.

In another aspect, the present invention provides a novel method of treating osteoarthritis, comprising: administering to a patient in need thereof a therapeutically effective amount of d-HA of the present invention (e.g., clauses (A)-(G)) or a pharmaceutically acceptable salt thereof.

In another aspect, the d-HA is administered via intra-articular injection.

In another aspect, the d-HA is administered to at least one knee, hip, shoulder, elbow, wrist, ankle, digit, or facet joint, of a patient.

The frequency of administration of a d-HA (alone) or in a composition will depend on its use. In the osteoarthritic setting it is beneficial to limit the number of treatments. Thus, the administration in this setting can be given weekly, bi-weekly, monthly, bi-monthly, quarterly, semi-annually, or even annually.

Examples of routes of administration include: intravenously, intradermally, intraarterially, intraperitoneally, intralesionally, intracranially, intraarticularly, intraprostatically, intrapleurally, intratracheally, intranasally, intrathecally, intravitreally, intravaginally, intrarectally, topically, intratumorally, intramuscularly, intraocularly, subcutaneously, subconjunctival, intravesicularlly, mucosally, intrapericardially, intraumbilically, intraocularally, orally, topically, locally, by inhalation, by injection, by infusion, by continuous infusion, by localized perfusion, via a catheter, via nebulizer, and via a lavage.

In another aspect, the present invention provides a novel method of slowing, attenuating, mitigating, and/or ameliorating the loss of bone mineral density in a vertebrate patient, comprising: orally administering a therapeutically effective amount of d-HA of the present invention (e.g., clauses (A)-(G)).

In another aspect, the present invention provides a novel method of slowing, attenuating, mitigating, and/or ameliorating the formation of osteophytes in a vertebrate patient, comprising: administering a therapeutically effective amount of d-HA of the present invention (e.g., clauses (A)-(U)).

In another aspect, the present invention provides a novel method of treating cancer, comprising: intravenously administering to a patient in need thereof a therapeutically effective amount of d-HA of the present invention (e.g., clauses (A)-(G)) prior to the administration of at least one cancer chemotherapeutic agent. The present invention also provides for using d-HA of the present invention (e.g., clauses (A)-(G)) as an entrainment and targeted delivery vehicle to transport said chemotherapeutic agent for use in intratumoral or intravenous injection in a patient.

In another aspect, the present invention provides a novel method for regulating vascular permeability in a patient having symptoms of or diagnosed with a disease or condition involving increased vascular permeability, comprising: administering a therapeutically effective amount of d-HA of the present invention (e.g., clauses (A)-(G)).

In another aspect, the present invention provides a novel method of preventing post-operative surgical adhesions of tissue in a patient, comprising: providing the tissue surfaces involved in the surgery with a hydrolyzable coating, comprising: d-HA of the present invention (e.g., clauses (A)-(G)). The coating can be in the form selected from the group consisting of a gel, membrane, foam, and fiber. The coating can further comprise: a pharmacologically active agent.

The invention also relates to isolated or purified d-HA. The isolated or purified d-HA is a group of molecules (i.e., an isolated compound) whose deuterium levels are above naturally occurring levels. The isolated or purified d-HA can be obtained by techniques known to those of skill in the art.

Isolated means that the non-naturally occurring d-HA is purified (e.g., from the fermentation reaction mixture in which it was prepared). Examples of the purity of the isolated d-HA (can be more than one type of compound) include at least 50%, 55%, 60%, 65%, 70%, 75%, 80%, 85%, 90%, 95%, 96%, 97%, 98%, 99% and 99.9% with respect to non-d-HA components being present.

The invention also relates to mixtures of d-HA compositions, which means that more than one type of d-HA is present.

In another aspect, the invention provides an amount of a d-HA. The amount of d-HA can be separate from other components and/or non-deuterium enriched HA or such other components can be present. Examples of amounts include (a) at least 0.01, 0.02, 0.03, 0.04, 0.05, 0.1, 0.2, 0.3, 0.4, 0.5, to 1 mole, (b) at least 0.1 moles, and (c) at least 1 mole of the compound. Examples of amounts also include (a) at least a gram of a d-HA; (b) at least a kilogram; and, (c) at least a metric ton. The present amounts also cover lab-scale (e.g., gram scale), kilo-lab scale (e.g., kilogram scale), and industrial or commercial scale (e.g., multi-kilogram or above scale) quantities as these will be more useful in the actual manufacture of a d-HA composition for use in patients. Industrial/commercial scale refers to the amount of product that would be produced in a batch that was designed for field testing, formulation, sale/distribution to the public, etc.

In another aspect, compositions of the invention will typically contain at least $6 \times 10^{19}$ molecules, and may, for example, contain at least $6 \times 10^{20}$ molecules, $6 \times 10^{21}$ molecules, $6 \times 10^{22}$ molecules or $6 \times 10^{23}$ molecules.

In another aspect, compositions of the invention contain at least 0.1 mole of at least one d-HA. Other examples of the amount of the d-HA include at least 0.2, 0.5, 1, 2, 3, 4, 5, 10, to 20 moles.

In another aspect, compositions of the invention contain at least a milligram of at least one d-HA. Other examples of the amount of the d-HA present include at least 1, 5, 10, 20, 30, 40, 50, 100, 500, to 1,000 grams.

In another aspect of the present invention, "comprising" is replaced by "consisting" in each of the previous aspects.

In another aspect of the present invention, "comprising" is replaced by "consisting essentially of" in each of the previous aspects.

The present invention may be embodied in other specific forms without departing from the spirit or essential attributes thereof. This invention encompasses all combinations of aspects of the invention noted herein. It is understood that any and all aspects of the present invention may be taken in conjunction with any other aspect or aspects to describe additional aspects. It is also to be understood that each individual element of the aspects is intended to be taken individually as its own independent aspect. Furthermore, any element of an aspect is meant to be combined with any and all other elements from any aspect to describe an additional aspect.

DEFINITIONS

All examples provided here are not intended to be limiting.

The use of "H" refers to the genus of hydrogen atoms, of any isotopic composition, i.e. $^1H$, $^2H$, or any combination thereof in any proportions. The use of "D" or "$^2H$" refers specifically to the deuterium isotope. Proportions described herein by percentages are percent by weight unless otherwise indicated. Natural abundance is approximately 0.0156%; the hand of man is needed to achieve significantly higher proportions (e.g., more than 1%).

Unless indicated otherwise, when a D is specifically recited at a position or is shown in a formula, this D represents a mixture of hydrogen and deuterium where the amount of deuterium is about 100% (e.g., the abundance of deuterium is from 90% to 100%). In certain aspects, the abundance of deuterium is from 97% to 100%. In certain aspects, abundance of deuterium is from 35% to 100%. The generic term 'd-HA' describes a HA polymer with deuterium at higher levels than natural abundance.

Compound refers to a quantity of molecules that is sufficient to be weighed, tested for their structural identity, and to have a demonstrable use (e.g., a quantity that can be shown to be active in an assay or a quantity that can be applied in a cosmetic setting in humans or a therapeutic setting in animal and human patients).

Molecular weight of the d-HA refers to the weight average molecular weight (i.e., $M_w$), unless otherwise indicated. The molecular weight of HA can be obtained by using a Multi-Angle static Light Scattering (MALS) detector (e.g., Wyatt Technology's DAWN® HELEOS® II) in combination with a size exclusion chromatography column. Alternatively, gel electrophoresis (with either agarose or polyacrylamide matrices), especially with the use of MALS-calibrated standards, can be used to assess the M, of HA.

Patient refers to humans or animals (e.g., canine, feline, equine, bovine, ovine, avian, caprine, camelid, mustelid, and exotics).

"Treating" or "treatment" covers the treatment of a disease-state in a patient, and includes: (a) preventing the disease-state from occurring in a patient, in particular, when such patient is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

EXAMPLES

The following examples of synthesizing deuterium-enriched d-HA are meant to illustrate, not limit, the present invention.

Example 1

Deuterium-enriched HA (e.g., d-HA, d-HA$_B$, d-HA$_{B1}$, d-HA$_1$, and d-HA$_2$) can be synthesized from pre-existing deuterium-labeled glucuronic acid and N-acetylglucosamine building blocks or from common sugar sources that would be converted into these building blocks during bacterial or fungal fermentation. For example, HA synthases synthesize HA in vitro from UDP-sugars (uridine diphosphate) according to the following equation:

$$n\text{UDP-GlcUA} + n\text{UDP-GlcNAc} \rightarrow 2n\text{UDP} + [\text{GlcUA-GlcNAc}]_n.$$

For d-HA labeled in the anomeric or other non-anomeric positions, the UDP-sugar precursors already have these positions labeled by deuterium. The labeled UDP-sugar building blocks arise from biosynthetic conversion of deuterium-labeled glucose (or other carbon source) into the UDP-N-acetylglucosamine (UDP-GlcNAc) and UDP-glucuronic acid (UDP-GlcUA) during fermentation.

For a review of various fermentation methods for producing HA (and also for deuterium-enriched HA such as d-HA, d-HA$_B$, d-HA$_{B1}$, d-HA1 and d-HA2 when a deuterated feedstock such as deuterium-enriched carbon source such as glucose or sucrose), see Boeriu, C. G., et al., International Journal of Carbohydrate Chemistry 2013, Article ID 627967 (http:dx.doi.org/10.1155/2013/624967), the contents of which are incorporated herein in their entirety.

Example 2

Deuterium-enriched HA (e.g., d-HA, d-HA$_B$, d-HA$_{B1}$, d-HA$_1$, and d-HA$_2$) can be formed via a fermentation process using known microbial strains including those derived from natural isolates including *Streptococcus* Group C (e.g., *S. zooepidemicus, equi, equisimilis, uberis*, etc) or *Streptococcus* Group A (*S. pyogenes*), or *Pasteurella multocida* (or related *A. vibacterium* allies) or virus-infected *Chlorella* algae as well as their artificially engineered derivative progeny, or recombinant versions with HA synthase genes in foreign hosts such as *Bacillus subtilis, Escherichia coli, Enterococcus, Lactobacillus* sp., or *Agrobacterium* sp, yeasts, fungi, or algae. The source of the HA is not the important aspect of this current invention, but rather the isotopic deuterium label in the HA chain. By fermenting in the presence of deuterated feedstock (e.g., deuterated glucose or other carbon source), one can produce deuterium-enriched HA. Other fungal and bacterial strains capable of producing HA in commercially useful quantities are also known to those skilled in the art.

Strains of *B. subtilis* suitable for HA fermentation are available from Novozymes Biopharma US (or DK A/S). Examples of such strains include those described in U.S. Pat. No. 7,811,806, the contents of which are incorporated herein in their entirety. For example, see strains TH1, RB161, RB163, RB187, RB197, and RB200, all of which were fermented using sucrose. The selection of a strain of *Streptococcus equi* that produces HA is described by Kim, J.-H., et al., *Enzyme and Microbial Technology* 1996, 19, 440-5, the contents of which are incorporated herein in their entirety. The use of a recombinant *Escherichia coli* strain to produce HA is described by Yu, H. et al., *Metabolic Engineering* 2008, 10, 24-32, the contents of which are incorporated herein in their entirety. The modification of *Agrobacterium* sp. ATCC 31749 to produce HA was described by Mao, Z. et al., *Biotechnology Progress* 2007, 23, 1038-42, the contents of which are incorporated herein in their entirety.

Use of a deuterated carbon source, such as deuterated sucrose will provide deuterium-enriched HA. Examples of deuterated sucrose include (β-D-[6,6'-$^2$H$_2$]fructofuranosyl α-D-glucopyranoside)([6,6'-$^2$H$_2^{fru}$]sucrose) and (β-D-[UL-$^2$H$_7$]fructofuranosyl α-D-[UL-$^2$H$_7$]glucopyranoside)([UL-$^2$H$_{14}$]sucrose), both of which are available from Omicron Biochemicals Inc. One can also use deuterated glucose as a carbon source. Examples include D-glucose-6,6-d$_2$, which is available from Sigma-Aldrich. Other deuterated glucoses could be used including D-glucose-1-d$_1$ D-glucose-1,2,3,4,5, 6,6-d$_7$ or D-glucose-d$_{12}$, which are also available from Sigma-Aldrich or Isotec. Deuterated fructose can also be used as a carbon source.

Finally, it is believed that the incorporation of deuterium from 6-deuterated glucose into the HA occurs via three-carbon fragments, e.g., deuterated glyceraldehyde 3-phosphate and/or dihydroxyacetone phosphate, which are produced from D-glucose during fermentation. Gluconeogenesis can also use oxaloacetate, a four-carbon fragment, as an intermediate for conversion into phosphoenolpyruvate. Thus, the skilled person could introduce the deuterium-labeled three carbon fragments or four carbon fragment or other deuterium-labeled feedstocks appropriate for gluconeogenesis into the fermentation to produce the deuterium-labeled UDP-sugar building blocks needed to make d-HA. Deuteration of these three starting materials can be achieved through deuterium exchange, e.g., contacting glyceraldehyde 3-phosphate and/or dihydroxyacetone phosphate and/or oxaloacetate with NaOD (alternatively Et$_3$N, or other suitable base) in D$_2$O.

Example 3

Deuterium-Enriched HA Production and Stability Testing

Strain and Media
Strain: *Pasteurella multocida* subsp. *multocida* (ATCC® #15742)
Plate Media: 5% sheep's blood agar (Teknova B0142)
Liquid Media Base: Dulbecco's Modification of Eagle Medium (DMEM) (Corning #90-113-PB) with:
 NaHCO$_3$: 2.2 g/L
 L-glutamine: 200 mg/L At time of growth, the following were added:
FeSO$_4$: 5 mg/L
Glucose: 2 g/L
The following glucoses were used:
D-Glucose (G) (Amresco #0188)(natural abundance control; no extra deuterium)
D-Glucose-1-d$_1$ (G1) (Aldrich #310816, 98 atom % D)(expect deuterium-enriched HA with singly deuterated GlcUA and GlcNAc, 2 deuteriums per repeating unit)
D-Glucose-6,6-d$_2$ (G6) (Aldrich #282650, 98 atom % D)(expect deuterium-enriched HA with di-deuterated GlcNAc, 2 deuteriums per repeating unit; no deuterium is expected on GlcUA as the 6,6 hydrogens are lost during biosynthetic conversion of glucose to glucuronic acid)
D-Glucose-1,2,3,4,5,6,6-d$_7$ (G7) (Aldrich #552003, 97 atom % D)(expect HA disaccharides with hepta-deuterated GlcNAc and tetra-deuterated GlcUA-10 deuteriums per repeating unit)

Growth of HA-Producing Bacteria

*P. multocida* P1059 was streaked onto blood agar plates and incubated at 37° C. overnight. Small starter cultures of DMEM with all additions and D-glucose (G) were inoculated with several colonies from the blood agar plate and incubated with shaking at 37° C. for approximately 7 hours. These starter cultures were used to inoculate Erlenmeyer flasks containing DMEM liquid media at a 1:500 inoculation ratio, each with unlabeled or a different labeled glucose (G, G1, G6 or G7). Cultures were allowed to incubate, shaking, at 37° C. for ~16 hrs.

HA Purification

The microbial cells were removed by centrifugation (10,000×g, 30 min). Ethanol (3× volumes) was added to the clarified supernatant which led to the precipitation of the HA polymer. The HA polymer was harvested by centrifugation. The resulting pellet was washed with 70% ethanol and allowed to dry overnight. The pellet was resuspended in water with gentle vortexing. Butanol extraction (1:1) of the aqueous solution was followed by chloroform extraction (1:1). The aqueous portion with HA polymer was stored at −20° C. Any other HA polysaccharide purification method can be employed including those using ion exchange or tangential flow filtration steps as well as repeated or sequential treatments with any of the above methods.

HA Size Analysis by Agarose Gel Analysis

All agarose gel analysis was performed using 1% agarose 1×TAE buffer gels, 10 cm in length, and Select-HA® HiLadder and LoLadder size standards (Hyalose, LLC). Gels were run at 40 V until the Orange G (Sigma) dye front was approximately 1 cm from the end of the gel. To visualize HA, gels are soaked in a solution containing 0.005% Stains-All (Sigma) in 50% Ethanol (2-16 hrs) in the dark and destained with water in the dark. HA polymers stain blue with this dye.

Results

*Streptomyces* HA lyase Digestion Test for Polymer Identity

Digestion of the polymer was performed with testicular hyaluronidase (Sigma; buffer 50 mM ammonium acetate, pH 5.5, 37° C. overnight, digests polymer to 4, 6, 8, etc. monosaccharide units=HA4, HA6, HA8, etc respectively). Reactions were filtered through a 3 kDa MWCO ultrafilter (Amicon) and the flow-through was analyzed by liquid chromatography coupled to electrospray Fourier transform mass spectrometry (LC-FTMS) (Ref: L. Li et al, Analytical Chemistry, 84, 8822-8829. 2012).

HA Oligosaccharide Generation & LC-FTMS for Deuterium Incorporation Level

Digestion of the polymer was performed with testicular hyaluronidase (Sigma; buffer 50 mM ammonium acetate, pH 5.5, 37° C. overnight, digests polymer to 4, 6, 8, etc. sugar units). Reactions were filtered through a 3 kDa MWCO ultrafilter (Amicon) and the flow-through was analyzed by LC-FTMS (Ref: L. Li et al, Analytical Chemistry, 84, 8822-8829. 2012). The expected additional mass due to deuterium addition were observed for "G1", "G6", and "G7" fed cultures in comparison to the natural abundance "G" control.

Figure 1:
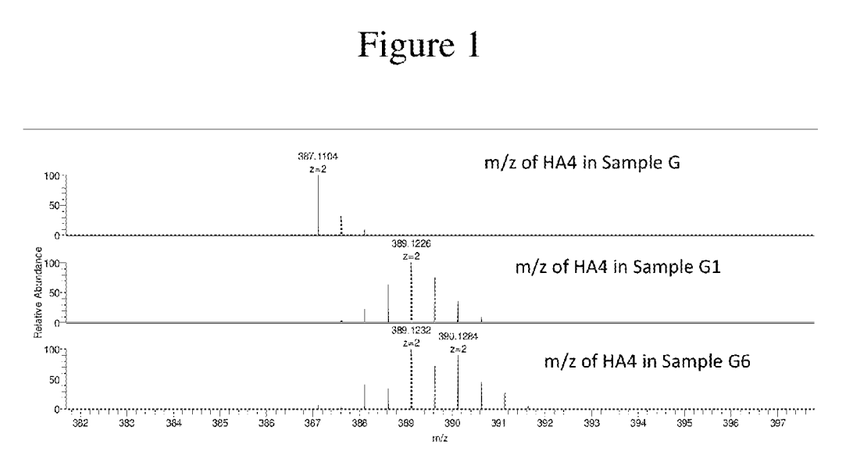

Basically, HA oligosaccharides in an enzymatic digest were subjected to a LC separation followed by electrospraying into a FT mass spectrometer. As an example, the data for the HA4 peak are shown in FIG. 1. The different isotopic distributions depend on the carbon source employed in the microbial growth step (i.e., natural, 1-d$_1$, or 6,6-d$_2$ glucose). The −2 ions (z=2) are observed (thus need to multiply by 2 to get the actual mass of the tetrasaccharide). Here for the tetramer (HA4), an increase of 4 Daltons is observed for both G1 and G6, as predicted. Specifically, natural HA, "G", had a mass of 776.236 while the d-HA versions, "G1" and "G6", had higher masses of 780.261 and 780.262, respectively, evidencing the synthesis of d-HA of the present invention. Similarly, all the other longer d-HA oligosaccharides observed (HA6, HA8, HA10) all had higher masses than the natural HA oligosaccharide counterparts due to their enrichment with deuterium.

The retention times (minutes) of the oligomers are listed in the table below.

| Sample | HA4 | HA6 | HA8 | HA10 |
| --- | --- | --- | --- | --- |
| G = D-(+)-Glucose | 5.22 | 5.59 | 5.77 | 5.98 |
| G1 = D-Glucose-1-d$_1$ | 5.24 | 5.58 | 5.78 | 5.92 |
| G6 = D-Glucose-6,6-d$_2$ | 5.22 | 5.58 | 5.78 | 5.93 |

The MWs of the HA4 and other longer oligomers, based on the most abundant ion peak observed in the mass spectrograms, are listed in the table below. The expected additional mass due to deuterium addition were observed for "G1", "G6", and "G7" fed cultures in comparison to the natural abundance "G" control.

| Sample | HA4 | HA6 | HA8 | HA10 |
| --- | --- | --- | --- | --- |
| G = D-(+)-Glucose | 776.236 | 1155.351 | 1534.465 | 1913.578 |
| G1 = D-Glucose-1-d$_1$ | 780.261 | 1161.387 | 1542.512 | 1923.637 |
| G6 = D-Glucose-6,6-d$_2$ | 780.262 | 1163.399 | 1544.524 | 1925.65 |

Oxidative Challenge of HA Polymers

The basic challenge conditions (initially based on Weissberger's oxidative system; *Neuro Endocrinol Lett.* 2012. 33 Suppl 3:151-4. 'Free-radical degradation of high-molar-mass hyaluronan induced by Weissberger's oxidative system: potential antioxidative effect of bucillamine'. Banasova M, Sasinkova V, Mendichi R, Perecko T, Valachova K, Juranek I, Soltes L. & *J Pharm Biomed Anal.* 2007. 44(5):1056-63. 'Degradation of high-molar-mass hyaluronan by an oxidative system comprising ascorbate, Cu(II), and hydrogen peroxide: inhibitory action of antiinflammatory drugs—naproxen and acetylsalicylic acid'. Soltes L, Stankovská M, Kogan G, Mendichi R, Volpi N, Sasinková V, Gemeiner P.) were as follows:
a. 0.1 µM CuCl$_2$
b. 100 µM ascorbic acid
c. 25 mM H$_2$O$_2$ All stock solutions were prepared in 0.15 M NaCl.

Figure 2:
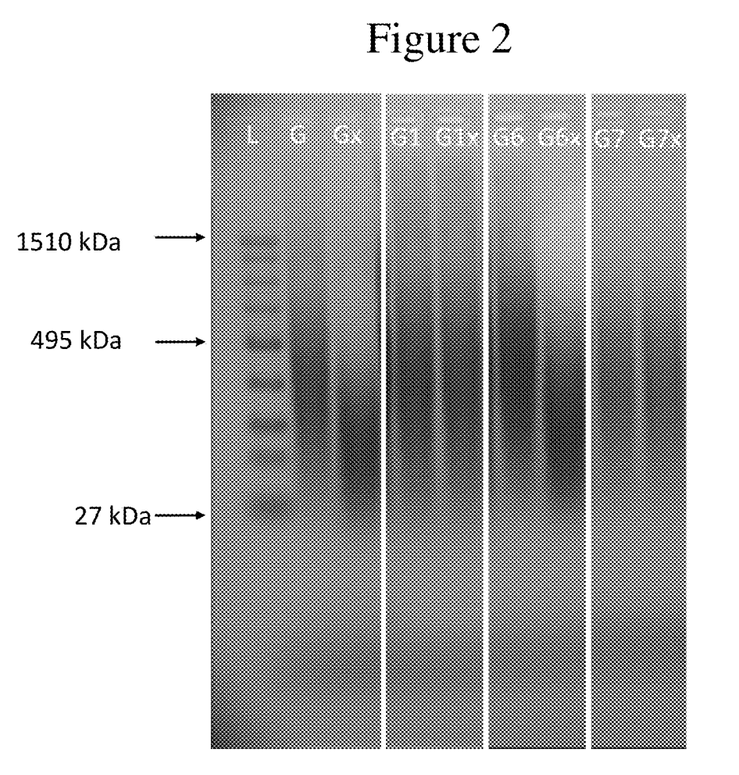
FIG. 2: Oxidative Challenge of Natural & [$^2$H]Glucose HA. The stability of deuterium-enriched HA according to the present invention was compared against unenriched HA.

FIG. 2 shows the results of an overnight test using the basic challenge conditions. In this example, agarose gel electrophoresis can separate HA according to size; the long polymers (i.e., chains with high molecular weight) run at the top of the gel compared to the smaller polymers (i.e., chains with low molecular weight) that migrate further into the gel. Streaks or smeared bands are observed in microbial HA because a wide range of polymer lengths are present in these samples and the gel image shows the summation of all polymer species present. Clear degradation of "G" and "G6" HA was observed (the streaks corresponding to stained polymer on the gel show only low molecular weight HA remains after oxidative challenge), but "G1" and "G7" stand up to the challenge (the streaks show high molecular weight HA, similar to the starting "G1" and "G7" HA). This finding is most likely due to these versions of d-HA enhancing stability of the bonds between the sugars (called glycosidic linkages) that hold the polymer together. Altering the behavior at carbon 1 via enrichment of deuterium (as in "G1" and "G7") prevents the fragmentation caused by the challenge. The "G6" version of d-HA, on the other hand, does not have deuterium at the glycosidic linkage thus is not protected.

Figure 3:
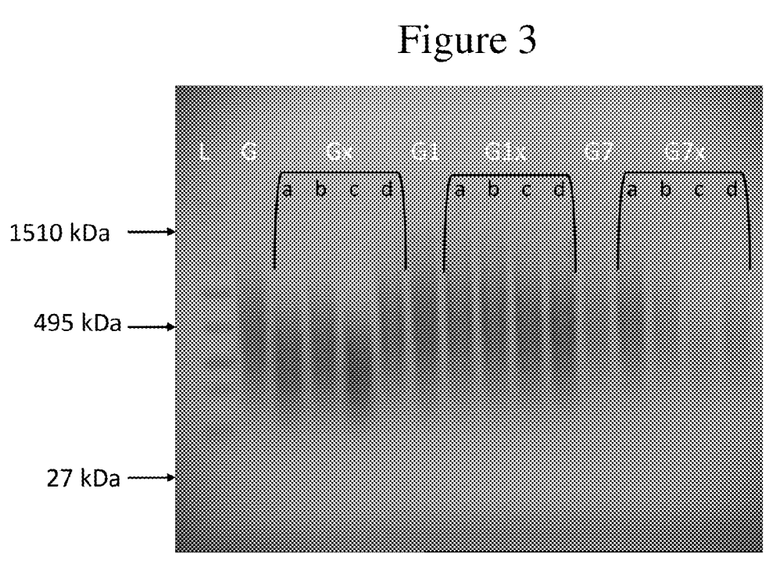
FIG. 3: Oxidative Challenge of Natural & [$^2$H]Glucose HA. The stability of deuterium-enriched HA according to the present invention was compared against unenriched HA.
Figure 4:
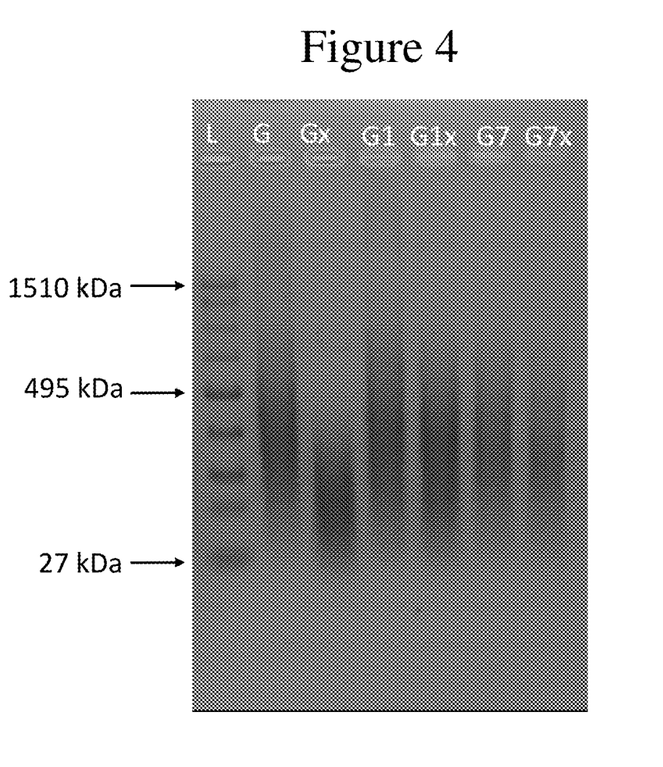
FIG. 4: Oxidative Challenge of Natural & [$^2$H]Glucose HA. The stability of deuterium-enriched HA according to the present invention was compared against unenriched HA.

The following abbreviations are used in FIG. 2 (and FIGS. 3-4):

L: HA Ladder standard;
G: Glucose (natural);
Gx: after oxidation challenge;
G1: Glucose-1-$d_1$;
G1x: Glucose-1-$d_1$ after oxidation challenge;
G6: Glucose-6,6-$d_2$;
G6x: Glucose-6,6-$d_2$ after oxidation challenge;
G7: Glucose-1,2,3,4,5,6,6-$d_7$; and,
G7x: Glucose-1,2,3,4,5,6,6-$d_7$ after oxidation challenge.

FIG. 3 shows the results of overnights tests using the following challenge conditions:

a: 0.1 µM $CuCl_2$, 100 µM ascorbic acid, 75 mM $H_2O_2$;
b: 0.1 µM $CuCl_2$, 100 µM ascorbic acid, 250 mM $H_2O_2$;
c: 1 µM $CuCl_2$, 1 mM ascorbic acid, 250 mM $H_2O_2$; and,
d: 0.1 µM $CuCl_2$, 100 µM ascorbic acid, 1.3 M $H_2O_2$.

"G1" and "G7" HA stand up to the challenge conditions (high MW streaks) when "G" HA degrades (low MW streaks).

FIG. 4 shows the results of overnight challenge test in 0.5 µM $CuCl_2$, 500 µM ascorbic acid, 125 mM $H_2O_2$. Once again "G1" and "G7" HA stand up to the challenge conditions (high MW streaks) when "G" HA degrades (low MW streaks).

Example 4

Osteoarthritis Compositions

Composition A:
A pre-filled sterile-packed syringe containing from 0.5-12 mL of d-HA in a sterile phosphate-buffered saline. The concentration of d-HA is from 0.2-5% w/w. The size of the d-HA is from about 50 kDa to about 5 MDa.

Composition B:
A pre-filled sterile-packed syringe containing from 0.5-12 mL of d-HA in a sterile phosphate-buffered saline. The concentration of d-HA is from 1-3% w/w. The size of the d-HA is from about 250 kDa to about 2.5 MDa.

Composition C:
the Compositions of A or B above where the d-HA is a chemically cross-linked d-HA.

Composition D:
the Compositions of A or B or C above where the d-HA is mixed or combined with other biomaterials (e.g., chitin, collagen, polylactic acid, plastics, ceramics, polymers, and/or cells).

Example 5

Ophthalmic Compositions

Composition A:
A composition of d-HA is formulated as eye drops at a concentration of from 0.05% to 1% w/w in a sterile ophthalmic solution known to those skilled in the art.

Composition B:
A composition of d-HA is formulated as eye drops at a concentration of from 0.1% to 0.5% w/w in a sterile ophthalmic solution known to those skilled in the art.

Composition C:
A composition of d-HA is formulated as eye drops at a concentration of from 0.15% to 0.25% w/w in a sterile ophthalmic solution known to those skilled in the art.

Composition D:
A composition of d-HA is formulated for intravitreal injection at a concentration of from 0.1% to 4% w/w in a sterile ophthalmic solution for injection known to those skilled in the art.

Example 6

Examples A-E are d-HA of the present invention wherein the hydrogens (shown or not shown) are un-enriched hydrogens (i.e., natural abundance of deuterium) and the shown deuteriums, D, are about 100% D.

-continued

Example 7

Example F is a d-HA of the present invention wherein the hydrogens (shown or not shown) are un-enriched hydrogens (i.e., natural abundance of deuterium) and the shown deuteriums, D, are about 100% D.

Numerous modifications and variations of the present invention are possible in light of the above teachings. It is therefore to be understood that within the scope of the appended claims, the invention may be practiced otherwise that as specifically described herein.

What is claimed is:

1. A deuterium-enriched hyaluronan, d-HA, of the formula:

wherein:
the d-HA has a molecular weight selected from about 15 kDa to about 10 MDa;
each non-$R^{D/D1}$ H is independently hydrogen or deuterium; and, each $R^D$ and $R^{D1}$ is independently hydrogen or deuterium, provided that at least 1% of the total number of $R^D$ and $R^{D1}$ groups present are D:
wherein d-HA is selected from: d-HA$_1$, d-HA$_{B1}$, F, and d-HA$_2$, or a pharmaceutically acceptable salt thereof, d-HA$_1$ d-HA$_{B1}$

F; and, d-HA$_2$

2. The d-HA of claim 1, wherein the d-HA is of formula d-HA$_1$:

or a pharmaceutically acceptable salt thereof;
wherein:
each non-$R^{D1}$ H is independently hydrogen or deuterium; and, each $R^{D1}$ is independently hydrogen or deuterium, provided that at least 1% of the $R^{D1}$ groups present are D.

3. The d-HA of claim 1, wherein the d-HA is of formula d-HA$_{B1}$:

or a pharmaceutically acceptable salt thereof;
wherein:
each non-$R^{D1}$ H is independently hydrogen or deuterium; and,
each $R^{D1}$ is independently hydrogen or deuterium, provided that at least 1% of the $R^{D1}$ groups present are D.

4. The d-HA of claim 1, wherein the d-HA is of formula F:

or a pharmaceutically acceptable salt thereof.

5. The d-HA of claim 1, wherein the d-HA is of formula d-HA$_2$:

or a pharmaceutically acceptable salt thereof;
wherein:
each non-$R^D$ H is independently hydrogen or deuterium; and,
each $R^D$ is independently hydrogen or deuterium, provided that at least 1% of the $R^D$ groups present are D.

6. The d-HA of claim 1, wherein the molecular weight is selected from about 0.1 MDa to about 5 MDa.

7. The d-HA of claim 1, wherein the molecular weight is selected from about 0.5 MDa to about 3 MDa.

8. The d-HA of claim 1, wherein the molecular weight is about 1-2.5 MDa.

9. The d-HA of claim 1, wherein the molecular weight is selected from about 15 kDa to about 100 kDa.

10. The d-HA of claim 1, wherein the molecular weight is selected from about 15 kDa to about 35 kDa.

11. The d-HA of claim 1, wherein at least 5% of the total number of $R^D$ and/or $R^{D1}$ groups present are D.

12. The d-HA of claim 1, wherein at least 10% of the total number of $R^D$ and/or $R^{D1}$ groups present are D.

13. The d-HA of claim 1, wherein at least 20% of the total number of $R^D$ and/or $R^{D1}$ groups present are D.

14. The d-HA of claim 1, wherein at least 30% of the total number of $R^D$ and/or $R^{D1}$ groups present are D.

15. The d-HA of claim 1, wherein at least 40% of the total number of $R^D$ and/or $R^{D1}$ groups present are D.

16. The d-HA of claim 1, wherein at least 50% of the total number of $R^D$ and/or $R^{D1}$ groups present are D.

17. The d-HA of claim 1, wherein at least 60% of the total number of $R^D$ and/or $R^{D1}$ groups present are D.

18. The d-HA of claim 1, wherein at least 70% of the total number of $R^D$ and/or $R^{D1}$ groups present are D.

19. The d-HA of claim 1, wherein at least 80% of the total number of $R^D$ and/or $R^{D1}$ groups present are D.

20. The d-HA of claim 1, wherein at least 90% of the total number of $R^D$ and/or $R^{D1}$ groups present are D.

21. A composition for treating osteoarthritis, comprising: a therapeutically effective amount of a d-HA of the formula:

or a pharmaceutically acceptable salt thereof, wherein:
the d-HA has a molecular weight selected from about 15 kDa to about 10 MDa;
each non-$R^{D/D1}$ H is independently hydrogen or deuterium; and,
each $R^D$ and $R^{D1}$ is independently hydrogen or deuterium, provided that at least 1% of the total number of $R^D$ and $R^{D1}$ groups present are D;
and a pharmaceutically acceptable excipient, wherein the composition is suitable for injection into the joint of a patient.

22. The composition of claim 21, wherein the joint is selected from the knee, hip, shoulder, wrist, ankle, elbow, digit, and facet joint.

23. The composition of claim 21, wherein the joint is the knee.

24. An ophthalmic composition, comprising: a d-HA of the formula:

or a pharmaceutically acceptable salt thereof, wherein:
the d-HA has a molecular weight selected from about 15 kDa to about 10 MDa;

each non-$R^{D/D1}$ H is independently hydrogen or deuterium; and, each $R^D$ and $R^{D1}$ is independently hydrogen or deuterium, provided that at least 1% of the total number of $R^D$ and $R^{D1}$ groups present are D;

and a pharmaceutically acceptable excipient, wherein the composition is suitable for injection or application in a patient's eye.

25. The composition of claim 24, wherein the composition is useful for treating age-related macular degeneration.

26. The composition of claim 24, wherein the composition is useful for injection as a vitreous supplement and/or replacement.

\* \* \* \* \*